United States Patent
Krishnan et al.

(10) Patent No.: US 7,529,394 B2
(45) Date of Patent: May 5, 2009

(54) CAD (COMPUTER-AIDED DECISION) SUPPORT FOR MEDICAL IMAGING USING MACHINE LEARNING TO ADAPT CAD PROCESS WITH KNOWLEDGE COLLECTED DURING ROUTINE USE OF CAD SYSTEM

(75) Inventors: Arun Krishnan, Exton, PA (US); Jonathan Stoeckel, Exton, PA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 681 days.

(21) Appl. No.: 10/877,263

(22) Filed: Jun. 25, 2004

(65) Prior Publication Data
US 2005/0010445 A1    Jan. 13, 2005

Related U.S. Application Data

(60) Provisional application No. 60/483,559, filed on Jun. 27, 2003.

(51) Int. Cl.
*G06K 9/00* (2006.01)

(52) U.S. Cl. .................. 382/128; 128/922; 600/408; 700/182; 706/14

(58) Field of Classification Search ............. 382/128, 382/130, 131, 132, 159, 100, 155; 128/922; 600/408, 414; 706/14, 15, 16, 20, 22, 919; 701/58, 59; 700/182
See application file for complete search history.

(56) References Cited

U.S. PATENT DOCUMENTS

| | | | |
|---|---|---|---|
| 5,586,160 A | * | 12/1996 | Mascio .................. 378/37 |
| 6,198,838 B1 | * | 3/2001 | Roehrig et al. ............. 382/132 |
| 6,738,499 B1 | * | 5/2004 | Doi et al. .................... 382/128 |
| 2002/0070970 A1 | | 6/2002 | Wood et al. |
| 2002/0076091 A1 | * | 6/2002 | Wang ........................ 382/132 |
| 2003/0165262 A1 | * | 9/2003 | Nishikawa et al. .......... 382/128 |

FOREIGN PATENT DOCUMENTS

| | | |
|---|---|---|
| JP | 6-343627 | 12/1994 |
| JP | 2000-501869 | 2/2000 |
| JP | 2001-503644 | 3/2001 |
| WO | WO 01/71660 A2 | 9/2001 |

OTHER PUBLICATIONS

Article entitled "Neural-Knowledge Base Object Detection in Hybrid Lung Nodule Detection (HLND) System" by Chiou et al., pp. 4180-4185.
Article entitled "Computerized Radiographic Mass Detection—Part II: Decision Support by Featured Visualization and Modular Neural Networks" by Li et al. pp. 302-313.
Article entitled Incremental Learning in a Multilayer Neural Network as an Aid to Alzheimer's Disease Diagnosis by Chan et al. pp. 1-4.
Article entitled "Automatic Image Segmentation and Classification Using On-line Shape Learning" by Lee et al., pp. 64-70.
Japanese Office Action dated Feb. 5, 2009.

* cited by examiner

*Primary Examiner*—Anand Bhatnagar

(57) ABSTRACT

CAD (computer-aided decision) support systems, methods and tools for medical imaging are provided, which use machine learning classification for automated detection and marking of regions of interest in medical images. Machine learning methods are used for adapting/optimizing a CAD process by seamlessly incorporating physician knowledge into the CAD process using training data that is obtained during routine use of the CAD system.

22 Claims, 4 Drawing Sheets

CAD (COMPUTER-AIDED DECISION) SUPPORT FOR MEDICAL IMAGING USING MACHINE LEARNING TO ADAPT CAD PROCESS WITH KNOWLEDGE COLLECTED DURING ROUTINE USE OF CAD SYSTEM

CROSS-REFERENCE TO RELATED APPLICATION

This application claims priority to U.S. Provisional application Ser. No. 60/483,559, filed on Jun. 27, 2003, which is fully incorporated herein by reference.

TECHNICAL FIELD OF THE INVENTION

The present invention relates generally to CAD (computer-aided decision) support systems, methods and tools, which use machine learning classification to provide automated decision support by detecting, diagnosing and marking of regions of interest in medical images. More specifically, the present invention relate to CAD support systems, methods and tools, which use machine learning methods that can adapt/optimize a CAD process by seamlessly incorporating physician knowledge into the CAD process using training data that is obtained during routine use of the CAD support system.

BACKGROUND

In the field of medical imaging, various systems have been developed for generating medical images of various anatomical structures of individuals for the purpose of screening and evaluating medical conditions. These imaging systems include, for example, CT (computed tomography) imaging, MRI (magnetic resonance imaging), X-ray systems, ultrasound systems, PET (positron emission tomography) systems, etc. Each imaging modality may provide unique advantages over other modalities for screening and evaluating certain types of diseases, medical conditions or anatomical abnormalities, including, for example, colonic polyps, aneurisms, lung nodules, calcification on heart or artery tissue, cancer micro calcifications or masses in breast tissue, and various other lesions or abnormalities.

For example, as is well known in the art, CT (computed tomography) imaging systems can be used to obtain a set of cross-sectional images or 2D "slices" of a ROI (region-of-interest) of a patient for purposes of imaging organs and other anatomies. The CT imaging modality is commonly employed for purposes of diagnosing disease because such modality provides a more precise image that illustrates the size, shape, and location of various anatomical structures such as organs, soft tissues, and bones, and also enables a more accurate evaluation of lesions and abnormal anatomical structures such as cancer, polyps, etc.

One conventional method that physicians, clinicians, radiologists, etc, use for detecting, diagnosing or otherwise evaluating medical conditions is to manually review hard-copies (X-ray films, prints, photographs, etc) of medical images that are reconstructed from an acquired image dataset, to discern characteristic features of interest. For example, CT image data that is acquired during a CT examination can be used to produce a set of 2D medical images (X-ray films) that can be viewed to identify potential abnormal anatomical structures or lesions, for example, based upon the skill and knowledge of the reviewing physician, clinician, radiologist, etc. For example, a mammogram procedure may produce medical images that include normal anatomical structures corresponding to breast tissue, but a trained radiologist may be able identify small lesions among these structures that are potentially cancerous. However, a trained radiologist, physician or clinician may misdiagnose a medical condition such as breast cancer due to human error.

Accordingly, various image data processing systems and tools have been developed to assist physicians, clinicians, radiologists, etc, in evaluating medical images to diagnose medical conditions. For example, computer-aided detection/diagnosis tools have been developed for various clinical applications to provide computer-assisted detection/diagnosis of medical conditions in medical images. In general, these CAD systems employ image data processing methods to automatically detect/diagnose possible lesions and other abnormal anatomical structures such as colonic polyps, aneurisms, lung nodules, calcification on heart or artery tissue, micro calcifications or masses in breast tissue, etc. More specifically, conventional CAD tools include methods for analyzing image data to automatically detect regions of features of interest in the image data which are identified as being potential lesions, abnormalities, disease states, etc. When the processed image data is rendered and displayed, the detected regions or features in the displayed image are "marked" or otherwise highlighted to direct the attention of the radiologist to the potential medical conditions.

Although CAD systems can be very useful for diagnostic/decision support assistance, the accuracy of the CAD system will vary depending on the manner in which the CAD process is programmed. In general, CAD systems can be implemented using "expert systems" in which the CAD process is developed and derived from a set of binary logic classification rules dictated by a human expert and translated into code, or trained using knowledge that is otherwise acquired heuristically. Unfortunately, expert systems which use binary logic classification rules or heuristic learning methods for developing the CAD process are inherently subjective to the expert developer and, consequently such systems are prone to errors due to the subjective nature of the design.

Moreover, with these conventional systems, human domain experts must learn and understand the reasons for classification errors and then manually update the classification rules to provide an acceptable level of accuracy. As such, these conventional methods are costly to implement and maintain due to the significant time and expense that is required for human experts to understand/learn the errors and generate/modify the appropriate rules to obtain more accurate detection results.

Furthermore, CAD systems can be implemented using principle (machine) learning classification methods, wherein an "off line" learning process can be used to train/build one or more classifiers for the CAD process using training data that is learned from a large database of previously diagnosed/labeled cases. Although the performance of the classifiers may be adequate when tested with the training data used to build the classifiers, the run-time performance of such classifiers can be poor when deployed in a CAD system when analyzing information that was not included in the original set of learning data.

For the above conventional programming paradigms, the CAD process may provide sub-optimal and generate incorrect results. For instance, the results of a CAD analysis can include "false positives" by incorrectly marking normal regions, or the CAD analysis may result in "unmarked" but nonetheless abnormal regions. In such instances, the physician's reliance on incorrect CAD marks could result in significant/substantial changes in a patient management process due to extra testing or biopsies, time lost by the radiologist, increased healthcare costs, trauma to the patient, and lead to a lack of trust in computer-assisted diagnosis systems.

SUMMARY OF THE INVENTION

In general, exemplary embodiments of the invention include CAD (computer-aided decision) support systems, methods and tools, which use machine learning classification to provide automated decision support by detecting, diagnosing and marking of regions of interest in medical images. More specifically, exemplary embodiments of the invention include CAD support systems, methods and tools, which use machine learning methods that can adapt/optimize a CAD process by seamlessly incorporating physician knowledge into the CAD process using training data that is obtained during routine use of the CAD support system.

In one exemplary embodiment of the invention, a method for computer-aided decision (CAD) support for medical imaging comprises processing patient image data using a CAD process to detect potential regions of interest in the patient image data, presenting CAD results obtained from the CAD process for review by a user, obtaining training data based on user review of the CAD results, and adapting the CAD process using the training data.

In one exemplary embodiment of the invention, the CAD results can be presented to the user by displaying at least a portion of the image data with CAD marks for detected regions of interest, if any. In such instance, training data can be obtained by determining a user mark added by the user which indicates a region of interest that was not detected and marked with a CAD mark, and collecting image information for the region of interest associated with the user mark, or by determining a CAD mark that was accepted by the user during the user review and collecting image information for the region of interest associated with the accepted CAD mark, or by determining a CAD mark that was rejected by the user during the user review and collecting image information for the region of interest associated with the rejected CAD mark, or by collecting image information for regions of interest that were neither marked with a CAD mark nor marked with a user mark, or any combination thereof.

These and other exemplary embodiments, features and advantages of the present invention will be described or become apparent from the following detailed description of exemplary embodiments, which is to be read in connection with the accompanying drawings.

DETAILED DESCRIPTION OF EXEMPLARY EMBODIMENTS

In general, exemplary embodiments of the invention as described herein include computer-aided detection/diagnosis systems and tools (generally referred to herein as CAD systems) which use machine learning classification for automated detection/diagnosis and marking of regions of interest in medical images. Moreover, exemplary CAD systems and tools according to the invention use machine learning methods for adapting/optimizing the CAD process by seamlessly incorporating physician knowledge into the CAD process using training data that is obtained during routine use of the CAD system. Exemplary embodiments of the invention will be described herein with reference to FIGS. 1, 2, 3 and 4.

It is to be understood that the systems and methods described herein in accordance with the present invention may be implemented in various forms of hardware, software, firmware, special purpose processors, or a combination thereof. In one exemplary embodiment of the invention, systems and methods described herein can be implemented as software applications comprising program instructions that are tangibly embodied on one or more program storage devices (e.g., magnetic floppy disk, RAM, CD Rom, DVD, ROM and flash memory), and executable by any device or machine comprising suitable architecture.

It is to be further understood that because the constituent system modules and method steps depicted in the accompanying Figures can be implemented in software, the actual connections between the system components (or the flow of the process steps) may differ depending upon the manner in which the application is programmed. Given the teachings herein, one of ordinary skill in the related art will be able to contemplate these and similar implementations or configurations of the present invention.

Figure 1:
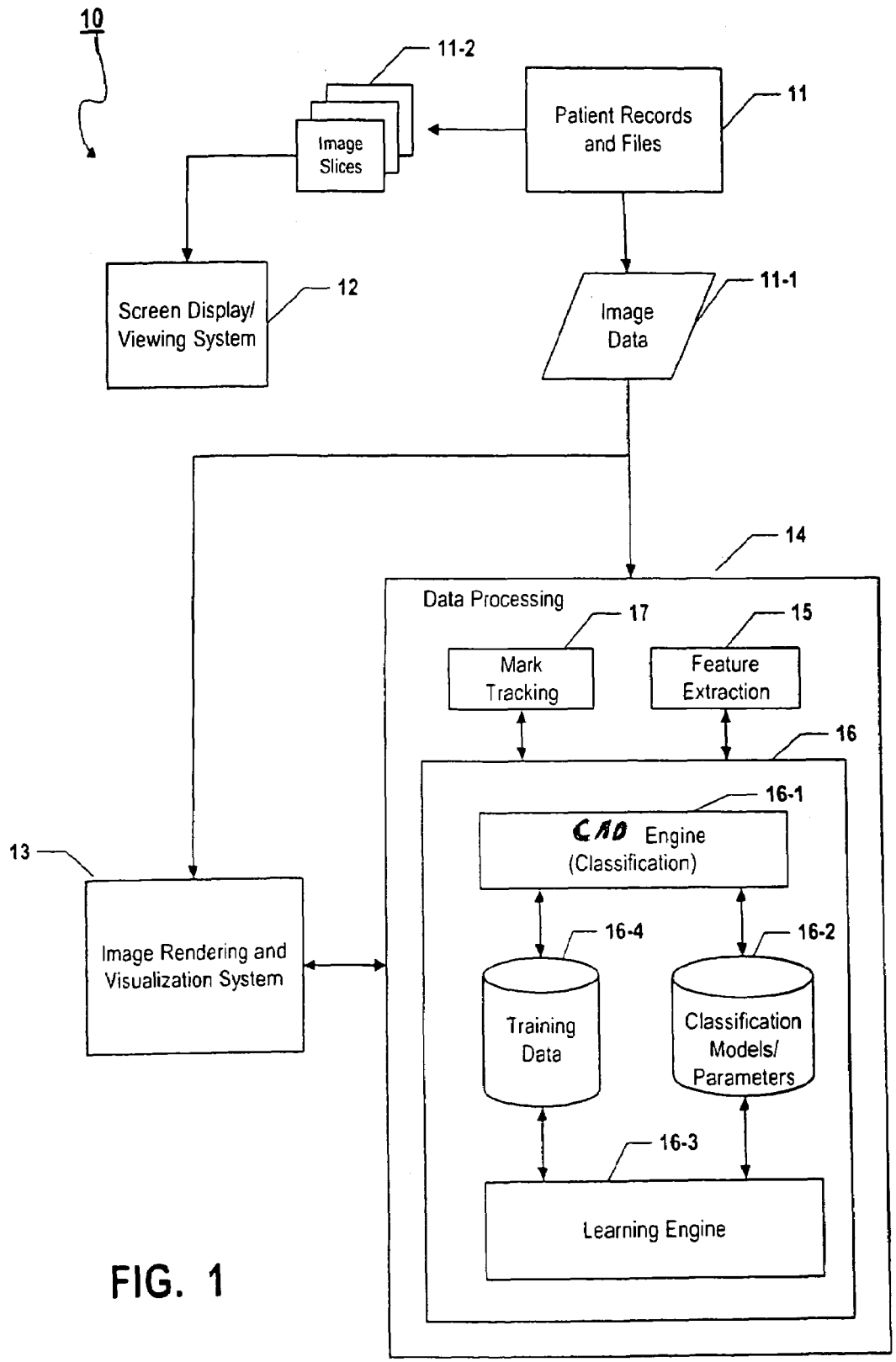
FIG. 1 is a block diagram of a system for analyzing patient medical records, which comprises a CAD tool that implements machine-learning classification methods for optimizing/adapting the CAD process from knowledge obtained during use of the CAD tool.

FIG. 1 is a block diagram of a system (10) for analyzing patient medical records according to an exemplary embodiment of the invention. In general, the system (10) comprises a repository of patient records and files (11), a screen display/viewing system (12), a 2D/3D image rendering and visualization system (13), and a data processing system (14) (or CAD system). As explained in further detail below, the CAD system (14) implements various methods for providing computer-aided decision support for detecting/diagnosing potential abnormal anatomical structures in the subject image dataset and for adapting/optimizing the CAD process using diagnostic knowledge that is acquired through user interaction with the CAD system (14) (e.g., knowledge that is obtained based on user acceptance and rejection of CAD marks during user review of detection results).

The patient data records and files (11) include patient image data and/or medical images for one or more subject patients. More specifically, the patient data records and files (1) may include digital image data (11-1) in the form of raw image data, such as raw CT data (radon data) which is acquired during a CT scan or raw data that is acquired using other imaging modalities. Moreover, the digital image data (11-1) may comprise one or more 2D slices or three-dimensional volumetric images, which are reconstructed from the raw image data and persistently stored. In addition, the patient data records and files (11) may comprise hard-copy 2D and/or 3D medical images (11-2) including X-ray films, prints, photographs, etc., of images that are reconstructed from acquired image data. For example, the medical images (11-2) may include a set of X-ray films including 2D slices of a patient that are reproduced from an image dataset acquired during a CT scan of a region of interest of the patient. It is to be understood that although exemplary embodiments of the invention may be described with reference to CT image data that is acquired using a computed tomography (CT) system, the present invention is applicable to other imaging modalities such as MRI, PET, etc. Image data can be 2D (e.g. X-ray Mammography images), 3D (e.g. CT, MRI, PET), 4D (Dynamic 3D MRI, multiple views of a beating heart acquired with a 3D Ultrasound probe), etc.

The screen display/viewing system (12) may be implemented using any system that is suitable for viewing reproduced medical images (11-2). For instance, the screen display/viewing system (12) may comprise a lighted screen apparatus that can be used by a physician, clinician, radiologist, etc., to view a plurality of X-rays films that are mounted on the apparatus, which are generated from an acquired image data set of multiple CT slices (11-2). The screen display/viewing system (12) may be implemented using any system that is suitable for scrolling through a plurality of reconstructed 2D slices, for example. The viewing system could also be a hardcopy, for example, a film-sheet that is viewed with a light box, or a paper printout, or other such means as known to those of ordinary skill in the art.

The image rendering and visualization system (13) may comprise any suitable system/tool/application that can process digital image data (11-1) of an acquired image dataset (or a portion thereof) to generate and display 2D and/or 3D images on a computer monitor. More specifically, the imaging system (13) may be any application that provides 3D/2D rendering and visualization of image data (11-1), and which executes on general purpose or specific computer workstation having a monitor. Moreover, the imaging system (13) comprises a GUI (graphical user interface), for example, which enables a user to navigate through a 3D image or a plurality of 2D slices.

The CAD system (14) comprises methods, functions and modules for processing digital image data (11-1) (and possible other non-image patient data) to provide computer-aided detection and diagnosis and other functions as described below. The CAD system (14) may comprise a CAD application or tool that executes on a general purpose computer or a computer with specialized hardware. The CAD system (14) receives and processes digital image data (11-1), which as noted above, may be in the form of raw image data, 2D-reconstructed data (e.g., axial slices), or 3D-reconstructed data (volumetric image data. or multiplanar reformats), 4D-reconstructed data, or other formats. The CAD system (14) implements methods for identifying, or at least localizing, certain features of interest, such as anatomical anomalies in the input image dataset (11-1) and adding markers (CAD marks) to the image data to indicate such features or regions. The CAD marks may be rendered as pointers (arrows, cross-hairs, etc,) that point to regions of interest having a potential abnormal structure or that point to a center location of a potential lesion or abnormality. Moreover, the CAD marks may be dotted lines that are formed around the perimeter or edge of a potential lesion or which generally encircle a region of interest that is detected/diagnosed as having a potential abnormal structure.

The data processing results (CAD results) of the CAD system (14) can be output to the image rendering/visualization system (13) for generating 2D and/or 3D renderings of image data in accordance with the processing results of system (14), such as superposition of markers, segmentation, color or intensity variations, and so forth as overlays on rendered image data. The CAD system (14) and image rendering and visualization system (13) may be implemented as a single application that executes in a computing system (e.g., workstation). Alternatively, the systems (13) and (14) may be independent tools that are distributed over a computer network, wherein known communication protocols such as DICOM, PACS, etc. are used for communicating between the systems (13) and (14) and transmitting image data (11-1) over the network.

In one exemplary embodiment of the invention such as depicted in FIG. 1, the CAD system (14) comprises a feature extraction module (15), a CAD module (16) and a mark tracking module (17). In general, the feature extraction module (15) includes methods for extracting relevant features or image parameters from image data (11-1) input to the CAD system (14). The CAD module (16) analyzes the extracted features and classifies the image data to automatically detect and mark potential regions of interest (e.g., abnormal anatomical structures) in the subject image dataset and output the CAD results for presentation to a user (e.g., display of image data with on overlay showing marked regions, if any, along with a probability of diagnosis, etc.) The mark tracking module (17) implements methods for tracking CAD marks and user marks during user review of detection results output by the CAD system (14) for purposes of acquiring expert knowledge or training data that can be used to adapt/optimize a CAD process implemented by the CAD module (16).

It is to be understood that methods implemented by the feature extraction module (15) will vary depending one the imaging domains (type(s) of image data (11-1)) supported by the CAD system (14), the types of classification methods used, as well as the type(s) of anatomical structures under consideration. For example, when detecting for breast cancer, various parameters related to optical density and contrast can be extracted to identify potential lesions in breast tissue. The types of feature extraction methods that can be implemented are well-known to those of ordinary skill in the art. It is to be understood that the feature extraction module (15) can implement segmentation methods for segmenting features or anatomies of interest by reference to known or anticipated image characteristics, such as edges, identifiable structures, boundaries, changes or transitions in colors or intensities, changes or transitions in spectrographic information, etc, using known methods.

In general, the CAD module (16) implements machine-learning classification methods for analyzing and classifying features/parameters of a subject image data set (11-1) to automatically detect and mark potential abnormal anatomical structures in the subject image dataset (11-1). More specifically, in the exemplary embodiment of FIG. 1, the CAD module (16) is implemented as knowledge-based expert system that provides automated detection (and possibly diagnosis) of regions of interest in image data. The CAD module (16) comprises a CAD process (16-1) (or CAD engine), a knowledge base (16-2), a learning process (16-3) and a repository (16-4) that stores various types of training data as described below.

The CAD process (16-1) implements one or more classification methods that utilize the knowledge base (16-2) for analyzing and classifying extracted features/parameters to detect potential regions of interest (e.g., abnormal anatomical structures). The knowledge base (16-2) maintains one or more trained classification models, parameters, and/or other data structures of learned knowledge, etc, which are used by the CAD process (16-1). Moreover, the learning engine (16-

3) implements one or more machine learning methods to enable optimization of the knowledge base (16-2) using training data that is collected during routine use of the CAD system (14) and persistently stored in repository (16-4).

It is to be appreciated that the training data is representative of a physician's diagnostic knowledge as acquired during use of the CAD system (14). More specifically, in one exemplary embodiment of the invention, the mark tracking module (17) includes one or more methods for tracking CAD marks and user marks during user review of detection results output from the CAD system (14), wherein training data can be obtained based on information associated with CAD marks that are accepted and/or rejected by the user or user marks that are included by a user, etc. Such data is generally representative of a physician's diagnostic knowledge, which can be incorporated into the CAD process. For example, system performance can be improved over time based upon "misses" of a previous classifier (e.g., the continuous learning component may be trained on errors or incorrect predictions made by the classifier). Various exemplary methods for collecting training data to optimize the CAD process will be described below with reference to FIG. 4, for example.

It is to be appreciated that the CAD system (14) can implement one or more of known classification methods for the detection process (16-1) including, for example, neural networks, decision trees, support vector machines, Bayesian networks, probabilistic reasoning, etc., and other classification methods that are known to those of ordinary skill in the art. It is to be appreciated that the classification methods implemented by the detection process (16-1) may be "black boxes" that are unable to explain their prediction to a user (which is the case if classifiers are built using neural networks, example). The classification methods may be "white boxes" that are in a human readable form (which is the case if classifiers are built using decision trees, for example). In other embodiments, the classification models may be "gray boxes" that can partially explain how solutions are derived (e.g., a combination of "white box" and "black box" type classifiers).

It is to be appreciated that the knowledge base (16-2) can include clinical domain knowledge base of information that is derived from various sources to support one or more clinical domains (e.g., heart imaging, breast imaging, etc.) For instance, the clinical domain knowledge (16-2) may include knowledge that is learned "off-line" from a large database of analyzed/labeled cases related to the clinical domain(s) to be supported by the CAD system (14). The clinical domain knowledge (16-2) may further include expert clinical knowledge that is input directly by an expert or information related to rules, regulations and/or guidelines associated with medical bodies or insurance companies, with regard to the supported clinical domain(s).

The learning engine (16-3) may implement one or more known machine learning methods that are capable of incorporating additional knowledge into the knowledge base (16-2) or otherwise adapting the information in the domain knowledge base (16-2) using training data derived from routing use of the CAD system (14). For example, reinforcement learning techniques may be used. Advantageously, machine learning functionality adds to the robustness of the CAD system (14) by enabling the classification process (16-1) to continually improve over time without costly human intervention.

It is to be understood that CAD systems and methods according to the present invention may be implemented as extensions to conventional CAD methods or other automated diagnostic methods for processing image data. Further, it is to be appreciated that the exemplary systems and methods described herein can be readily implemented with 3D medical imaging and CAD systems or applications that are adapted for a wide range of imaging modalities (CT, MRI, etc.) and diagnosis and evaluation of various abnormal anatomical structures or lesions such as colonic polyps, aneurisms, lung nodules, etc. In this regard, although exemplary embodiments may be described herein with reference to particular imaging modalities or particular anatomical features, nothing should be construed as limiting the scope of the invention.

Moreover, in other exemplary embodiments of the invention, in FIG. 1, the CAD system (14) can extract and analyze information (image parameters/features) from one or more imaging modalities data (11-1) (e.g., ultrasound image data, MRI data, NMR data, PET data, CT data, etc.) and (optionally) non-image data for analysis by the CAD process. In other words, the feature extraction module (15) may include one or more patient data extraction methods for extracting "non-image" patient data from structured and/or unstructured patient data records (11), which may be relevant for a clinical/image domain under consideration, and combining the image features/parameters and non-image features/parameters in a manner that is suitable analysis by the CAD process. Although the clinical non-image data may not pinpoint specific regions of potential abnormalities, for example, such non-clinical clinical data can be helpful overall in the CAD evaluation process. Indeed, data analysis/data mining methods may be implemented by the extraction module (15) for extracting relevant parameters from the all types of patient data records (11), and to deal with errors/inconsistencies/missing information in the patient records. For this purpose, in one exemplary embodiment of the invention, CAD system (14) may utilize the data mining methods and feature combination methods as described in commonly assigned and copending U.S. patent application U.S. Ser. No. 10/287,055, filed on Nov. 4, 2002, entitled "Patient Data Mining", which claims priority to U.S. Provisional Application Ser. No. 60/335,542, filed on Nov. 2, 2001, which are both fully incorporated herein by reference.

Figure 2:
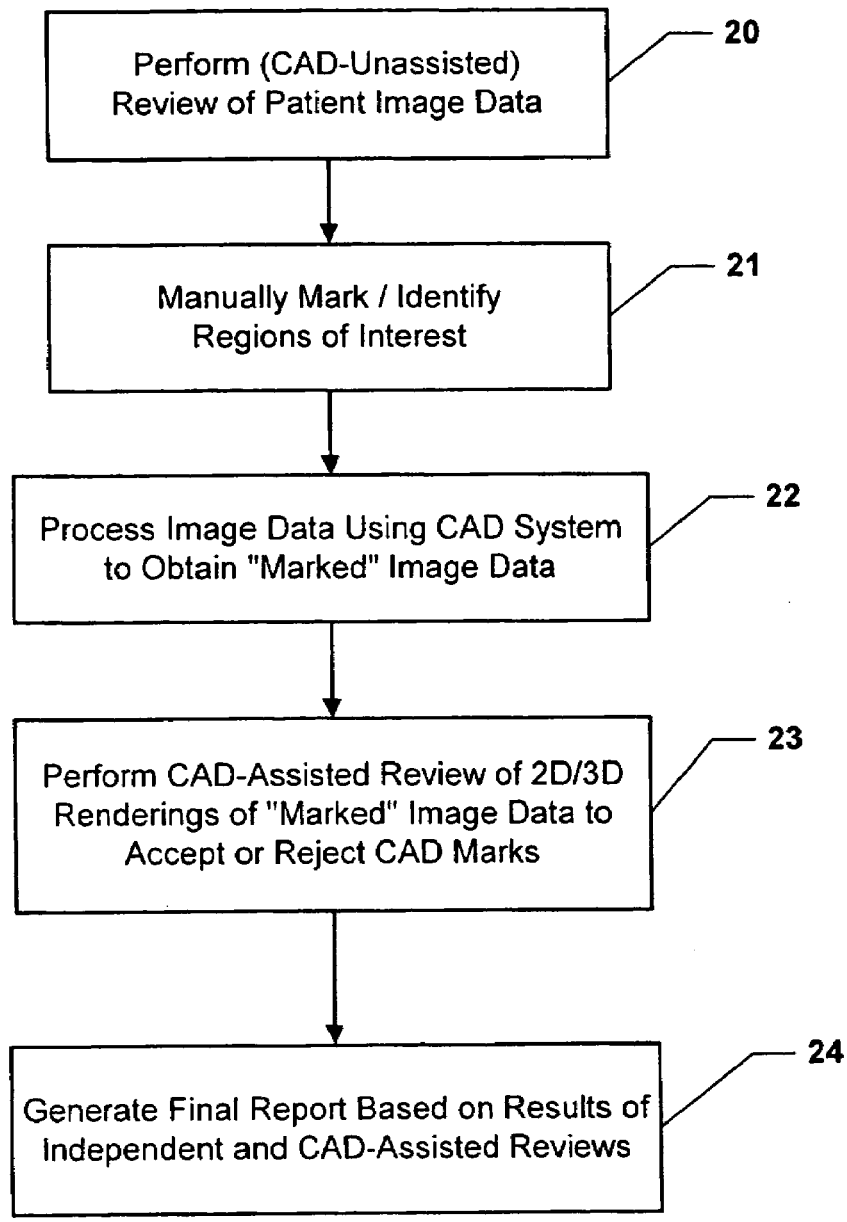
FIG. 2 is a flow diagram of a workflow process for physician review of patient medical records using the system of FIG. 1, according to an exemplary embodiment of the invention.

Referring now to FIG. 2, a flow diagram illustrates a workflow for physician review and analysis of patient image data according to an exemplary embodiment of the invention. For purposes of illustration, the exemplary method of FIG. 2 will be described with reference to the system of FIG. 1. Initially, a physician, clinician, radiologist, etc., will perform a preliminary (CAD-unassisted) review and analysis of patient image data of a subject patient (step 20) to identify potential abnormal anatomical structures or disease states. For example, in one embodiment of the invention, the physician could use the screen display/review system (12) (FIG. 1) to review one or more x-ray films of 2D image slices, which are generated from an image dataset acquired via a CT exam, for example.

In another exemplary embodiment, the physician could review 2D and/or 3D renderings of the image dataset, which are displayed on a computer monitor to identify possible abnormal features. For example, the physician can use the image visualization system (13) (FIG. 1) to render and display 2D and/or 3D images of the all or portions of the input image dataset, and navigate through the displayed images using a suitable GUI to identify potential abnormal features. In such case, the visualization system (13) simply constructs and displays 2D and/or 3D images for review by the physician, but does not perform CAD related functions to assist in the analysis, nor display images that are rendered and displayed based on CAD results.

Based on the initial review, the physician may manually mark or otherwise identify regions of interest in image data (step 21), which are believed by the physician to include (or to be) potential lesions or anatomical anomalies. Moreover, using related GUI functions for the visualization system (13), the physician may mark or otherwise highlight particular regions of the displayed 2D and/or 3D images. The physician may possibly generate a preliminary report of his/her initial findings based on the CAD-unassisted review of the patient image data. This report may comprise preliminary diagnostic decisions and findings of the physician, including references to particular regions (or features) of interest in the image data.

Thereafter, the physician will perform a CAD-assisted review of the patient data to verify or reconcile his/her preliminary findings. More specifically, in one exemplary embodiment of the invention, a CAD-assisted review commences by obtaining "marked" image data resulting from processing the image dataset (which was the subject of the preliminary review) using the CAD system to detect and mark potential lesions or other abnormal anatomical structures in the image data (step 22). The processing may be performed "off-line" prior to the first read or in the background during the first read, or such processing may occur after the first read by the user explicitly executing the CAD system (14) to process image data currently displayed (e.g., via system 13) for the CAD-unassisted review (with possible user marks inserted).

The physician will then perform a CAD-assisted review of the patient image data based on 2D and/or 3D renderings of the "marked" image data that are displayed on a display device (step 23). For example, the output of the CAD system (14) (e.g. "marked" image data) can be input to the image rendering/visualization system (13), which generates and displays one or more 2D and/or 3D medical images showing computer-generated marks (CAD marks), if any, based on the results of the CAD process. In other words, the displayed images may be marked or otherwise annotated with a localized identification of potential abnormalities that are detected by the CAD module (16). During the CAD-assisted review, the physician can interact with the system via a GUI by adding new user marks to the image data in regions of interest that the physician believes include potential abnormalities not found by the CAD process. Moreover, the physician may reject or otherwise delete CAD marks that were found by the CAD process, but which the physician believes are erroneous, or otherwise accept CAD marks that the physician believes are accurate. The user interaction (e.g., adding user marks and accepting/rejecting CAD marks) during user review of the detection results is tracked to obtain one or more of different types of training data to be used to optimize/adapt the CAD process, as described below.

Following the CAD-assisted review, the physician can augment his/her preliminary report based on the final diagnostic decision (step 24). This final diagnostic report may or may not be the same as the preliminary report, depending on whether the physician determines additional diagnostic information provided by the CAD tool to be significant. Following the final diagnostic report, the physician can recommend a course of further action, which can include no further action or further follow-up examinations or procedures.

Figure 3:
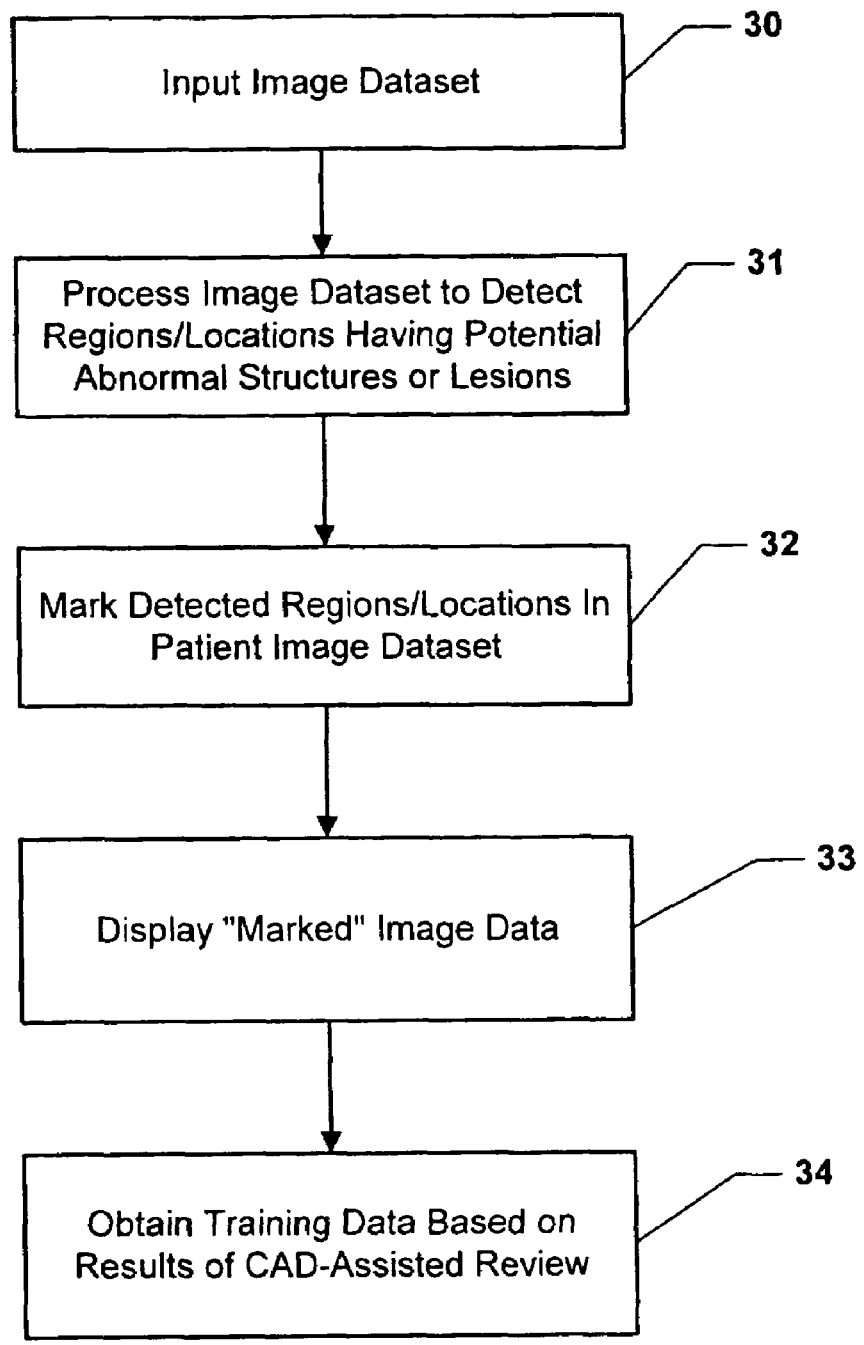
FIG. 3 is a flow diagram of a CAD method according to an exemplary embodiment of the invention.

FIG. 3 is a flow diagram that illustrates a CAD method according to an exemplary embodiment of the invention. In one embodiment of the invention, FIG. 3 depicts methods that are implemented for steps 22 and 23 of FIG. 2. In another embodiment of the invention, FIG. 3 illustrates a mode of operation of the CAD system (14) of FIG. 1. Referring to FIG. 3, an image dataset of a subject patient (and possible non-image data mined from the patient records as noted above) is input to the CAD system (step 30). The input image dataset is processed to detect and identify potential regions (or features) of interest, if any, in the image dataset having potential abnormal anatomical structures (step 31). It is to be understood that the CAD process (step 31) may be implemented using any method which is suitable for the imaging modality (e.g., CT) of the input image data and which is specifically or generally adapted for detecting/diagnosing anatomical abnormalities (e.g., cancer, polyps, nodules, etc.) that are under consideration. The CAD process will mark those regions of interest in the input image dataset, which are determined to be potential lesions or other abnormal structures.

Thereafter, the CAD results are presented to the user. For instance, the "marked" image dataset is output from the CAD module (step 33) and further processed for rendering and displaying 2D and/or 3D images showing the CAD marks (and possibly the previously inserted user marks that were made by the user during the user's initial CAD-unassisted review). During the CAD-assisted review, the CAD system implements a background method for obtaining training data resulting from the CAD-assisted review (step 34), which is subsequently used in a learning process to update the knowledge base used for the CAD process. Various types of training data that can be collected will now be discussed in further detail with reference to FIG. 4.

Figure 4:
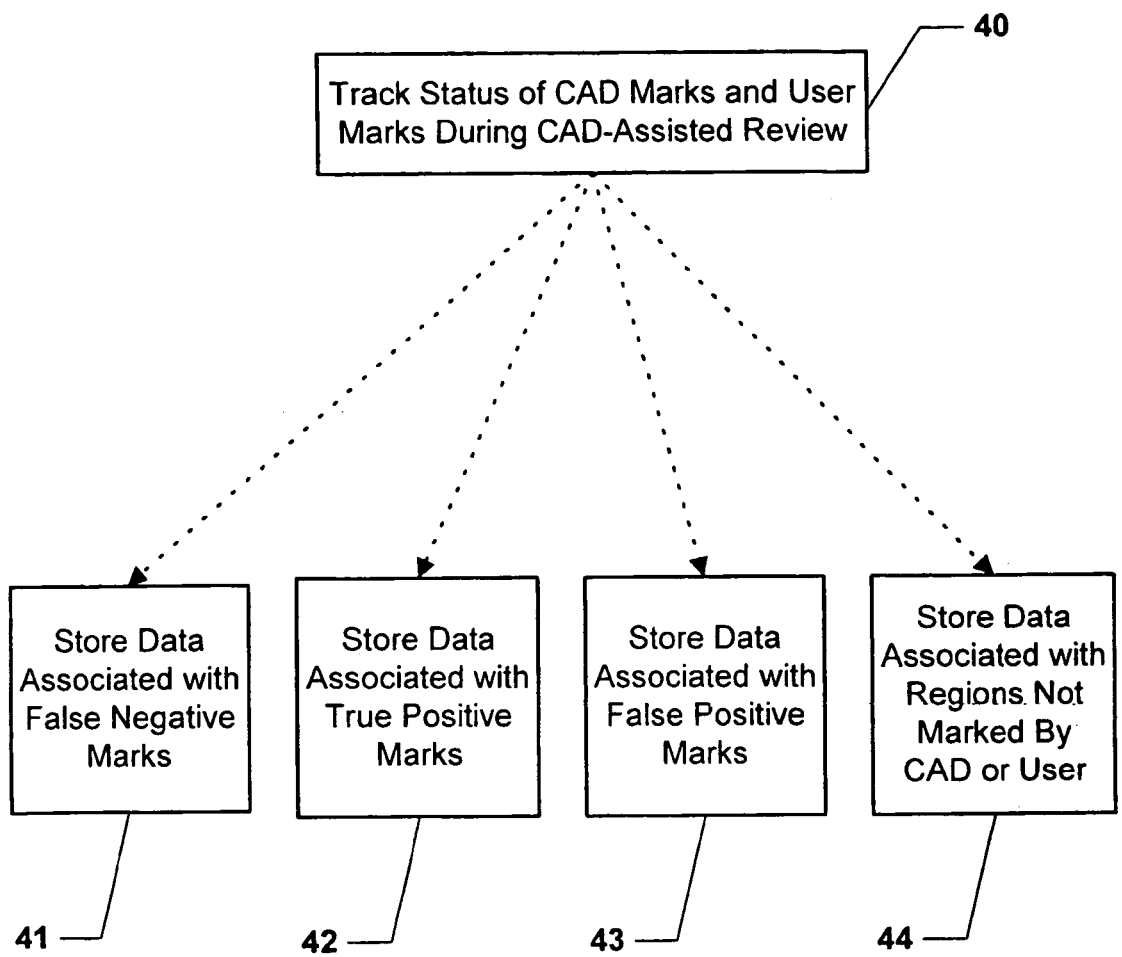
FIG. 4 is a flow diagram illustrating methods for collecting training data according to exemplary embodiments of the invention, which can be used for optimizing the CAD process.

FIG. 4 is a flow diagram illustrating methods for collecting training data according to exemplary embodiments of the invention, which can be used for optimizing the CAD process. In particular, FIG. 4 illustrates various modes of operation according to exemplary embodiments of the invention implementing step 34 in FIG. 3. More specifically, during the CAD-assisted review of the user, the CAD system (14) will track the status of the CAD marks (e.g., user acceptance or rejection of marks) and user marks (e.g., marks added by user but not found by CAD process) (step 40) and collect one or more types of training data (steps 41, 42, 43, and/or 44). The exemplary types of training data can be used singularly, or in various combinations, for use in adapting/optimizing the CAD process.

For instance, in one exemplary embodiment of the invention, the CAD system (16) will keep track of the CAD marks and user marks and determine which marks, if any, were found by the user during his/her independent read but were not found by the CAD process (referred to as "false negative" marks). The CAD system will then store data associated with such false negative marks as training data (step 41). The training data includes, for example, the locations of such false negative marks and other types of supporting data including the image sub-volume data and extracted features, etc. This type of training data can be used for allowing the CAD process to learn from its mistakes.

In another embodiment of the invention, the CAD system will keep track of the CAD marks and user marks and determine which marks, if any, were found by both the user during his/her independent read and the CAD process (referred to as "true positive" marks) (step 42), as well as any "false negative" marks (sep 41) as above. The CAD system will then store data associated with such "true positive" and "false negative" marks as training data. Again, the training data would include, for example, the locations of such false negative and true positive marks and other types of supporting data including the image sub volume data and extracted features, etc. This type of training data can be used to prevent biasing the CAD system towards its mistakes.

In another embodiment of the invention, the CAD system will keep track of the CAD marks and user marks and determine the marks, if any, that were found by the CAD process but rejected by the user ("false positive" marks) as well as any "false negative" marks as above. The false positive marks may be CAD marks that were placed on anatomical structures that resemble lesions or anomalies of interest. For instance, when diagnosing for cancer, false positive CAD marks may be added to regions that include scar tissues, which may have features similar to cancer. The CAD system will then store data associated with such "false positive" (step 43) and "false negative" marks (step 41) as training data. Again, the training data would include, for example, the locations of such false positive and false negative marks and other types of supporting data including the image sub volume data and extracted features, etc.

In another embodiment of the invention, the CAD system will keep track of the CAD marks and user marks and determine those "unmarked" regions that were not marked by the CAD process or the user, as well as the false positive and false negative marks, if any. The CAD system will then store data associated with the "unmarked" (step 44), "false positive" (step 43) and "false negative" marks (step 41) as training data. Again, the training data would include, for example, the locations of such unmarked regions, or false positive and false negative marks and other types of supporting data including the image sub volume data and extracted features, etc. This type of training data can be used for to prevent biasing the CAD system towards its mistakes and allow reinforcement of the knowledge base using training data associated with image data that is deemed not to contain abnormalities by the user and the CAD process.

It is to be appreciated that the training data can be used to adapt the knowledge base and incorporate more knowledge that is learned from the expert user interaction with the system. In other words, the adaptation is seamless (unsupervised training) because the training data is being collected in the background and the expert user may be unwittingly training the system by expanding the training data set. In other words, the expert user does not consciously train the system. The learning process can be implemented on a continuous basis were the knowledge base is updated with each set of training data collected so that each time the CAD is used, the models/parameters are updated. In another embodiment of the invention, the learning process is not executed until training data from a predetermined number of cases is collected. The frequency at which learning can be implemented can be varied depending on the experience of the users of the CAD system. For instance, it may not be desirable to perform continuous learning if the CAD system is being used by inexperienced users, who may not be experienced in viewing medical images. In such case, the added knowledge as captured in a training data set may be erroneous or inaccurate In other exemplary embodiments of the invention, a verification process may be implemented for evaluating the accuracy of updated/newly trained classifier(s) to determine the efficacy or accuracy of the classifier(s) for the CAD process. For example, the classifier(s) can be evaluated by processing actual training data of from previous cases with known outcomes, and then comparing the classification results against the expected or known outcomes to obtain an accuracy score. In such instance, if the accuracy score falls below a desired threshold, the classifier(s) will be rejected and the training process can be continued. If the classifier(s) pass evaluation, the updated/newly trained classifier(s) can be used.

It is to be appreciated that the methods described above for obtaining data during routine use of the CAD system are merely exemplary, and that one of ordinary skill in the art could readily envision other methods for obtaining or otherwise extracting training data based on routine use of the CAD system, which is indicative of the user's expert knowledge. For instance, rather than displaying a "marked" image and tracking a user's acceptance or rejection of CAD marks via GUI interaction, a CAD-assisted review may be performed in other ways, such as presenting the CAD results to a user via a printed image, in which case the user may review the printed copy and note his/her acceptance or rejection of the CAD results in his/her final report. In such instance, the CAD system can determine or otherwise infer user acceptance or rejection of the CAD results by analyzing information in the preliminary and final reports and reconciling any differences and/or similarities between such reports and the known CAD results.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A method for computer-aided decision (CAD) support in medical imaging, comprising:
    processing patient image data using a CAD process to detect potential regions of interest in the patient image data;
    presenting CAD results obtained from the CAD process for review by a user;
    receiving user-generated diagnosis that is based on the presented CAD results;
    collecting unsupervised training data in the background based on user-generated diagnosis of the CAD results; and
    adapting the CAD process using the collected unsupervised training data for subsequent processing of subsequent patient image data, wherein the frequency at which the collected unsupervised training data is used to adapt the CAD process is varied depending on a level of experience of the user and wherein the CAD process is based on offline training, the unsupervised training data collected in the background, and expert rules, regulations or guidelines.

2. The method of claim 1, wherein processing the patient image data using a CAD process comprises automatically extracting image parameters from the patient image data and classifying the parameters using a classification method, and wherein adapting the CAD process is performed using a machine learning process to retrain a classifier using the training data.

3. The method of claim 1, wherein presenting the CAD results comprises displaying at least a portion of the image data with CAD marks for detected regions of interest.

4. The method of claim 3, wherein obtaining training data comprises:
    determining a user mark added by the user which indicates a region of interest that was not detected and marked with a CAD mark; and
    collecting image information for the region of interest associated with the user mark.

5. The method of claim 3, wherein obtaining training data comprises:
    determining a CAD mark that was accepted by the user during the user review; and collecting image information for the region of interest associated with the accepted CAD mark.

6. The method of claim 3, wherein obtaining training data comprises:
determining a CAD mark that was rejected by the user during the user review; and
collecting image information for the region of interest associated with the rejected CAD mark.

7. The method of claim 3, wherein obtaining training data comprises collecting image information for regions of interest that were neither marked with a CAD mark nor marked with a user mark.

8. The method of claim 1, wherein adapting the CAD process using the training data comprises retraining the CAD process continuously or periodically.

9. The method of claim 1, further comprising obtaining training data based on results of a CAD-unassisted user review of the patient image data.

10. A computer-readable medium, tangibly embodying a computer program of instructions executable by the computer to perform method steps for providing computer-aided decision (CAD) support in medical imaging, the method steps comprising:
processing patient image data using a CAD process to detect potential regions of interest in the patient image data;
presenting CAD results obtained from the CAD process for review by a user;
receiving user-generated diagnosis that is based on the presented CAD results;
collecting unsupervised training data in the background based on user-generated diagnosis of the CAD results; and
adapting the CAD process using the collected unsupervised training data for subsequent processing of subsequent patient image data, wherein the frequency at which the collected unsupervised training data is used to adapt the CAD process is varied depending on a level of experience of the user and wherein the CAD process is based on offline training, the unsupervised training data collected in the background. and expert rules, regulations or guidelines.

11. The computer-readable medium of claim 10, wherein the instructions for processing the patient image data using a CAD process comprise instructions for automatically extracting image features from the patient image data and classifying the features using a classification method, and wherein the instructions for adapting the CAD process include instructions for using a machine learning process to rebuild a classifier using the training data.

12. The computer-readable medium of claim 10, wherein the instructions for presenting the CAD results comprise instructions for displaying at least a portion of the image data with CAD marks for detected regions of interest.

13. The computer-readable medium of claim 12, wherein the instructions for obtaining training data comprise instructions for:
determining a user mark added by the user which indicates a region of interest that was not detected and marked with a CAD mark; and
collecting image information for the region of interest associated with the user mark.

14. The computer-readable medium of claim 12, wherein the instructions for obtaining training data further comprise instructions for:
determining a CAD mark that was accepted by the user during the user review; and
collecting image information for the region of interest associated with the accepted CAD mark.

15. The computer-readable medium of claim 12, wherein the instructions for obtaining training data further comprise instructions for:
determining a CAD mark that was rejected by the user during the user review; and
collecting image information for the region of interest associated with the rejected CAD mark.

16. The computer-readable medium of claim 12, wherein the instructions for obtaining training data comprise instructions for collecting image information for regions of interest that were neither marked with a CAD mark nor marked with a user mark.

17. The computer-readable medium of claim 10, wherein the instructions for adapting the CAD process using the training data comprise instructions for retraining the CAD process continuously or periodically.

18. The computer-readable medium of claim 10, further comprising instructions for obtaining training data based on results of a CAD-unassisted user review of the patient image data.

19. A method for computer-aided decision (CAD) support, comprising:
obtaining CAD results from processing patient data using a CAD process;
obtaining user-generated diagnosis from a user, based on the obtained CAD results, comprising the results of (i) a user review of the patient data, or (ii) a user review of the CAD results, or (iii) both a user review of the patient data and the CAD results;
comparing the CAD results and the user-generated diagnosis; and
collecting unsupervised training data in the background based on the comparing results for adapting the CAD process for subsequent processing of subsequent patient data wherein the frequency at which the collected unsupervised training data is used to adapt the CAD process is varied depending on a level of experience of the user and wherein the CAD process is based on offline training, the unsupervised training data collected in the background, and expert rules, regulations or guidelines.

20. The method of claim 19, wherein comparing the CAD results and the user review results comprises determining a false positive CAD result, or a false negative CAD result, or a true positive CAD result, or any combination thereof.

21. The method of claim 19, wherein the CAD results comprise CAD marks for potential regions of interest detected by the CAD process, if any, in patient image data.

22. The method of claim 21, wherein the results of the user review of the CAD results comprise indications as to the user's acceptance or rejection of a CAD mark.

* * * * *